United States Patent [19]

Rebafka et al.

[11] Patent Number: 4,645,863

[45] Date of Patent: Feb. 24, 1987

[54] PROCESS FOR THE PREPARATION OF UNSATURATED ALCOHOLS AND/OR ESTERS THEREOF

[75] Inventors: Walter Rebafka, Hirschberg; Helmut Nickels, Mutterstadt, both of Fed. Rep. of Germany

[73] Assignee: BASF Aktiengesellschaft, Ludwigshafen, Fed. Rep. of Germany

[21] Appl. No.: 457,464

[22] Filed: Jan. 12, 1983

[30] Foreign Application Priority Data

Jan. 15, 1982 [DE] Fed. Rep. of Germany ....... 3200990

[51] Int. Cl.⁴ ..................... C07C 29/04; C07C 67/04; C07C 69/145
[52] U.S. Cl. .................................... 568/899; 560/241; 568/895
[58] Field of Search ................. 564/241; 568/895, 899

[56] References Cited

U.S. PATENT DOCUMENTS

| | | | |
|---|---|---|---|
| 3,523,108 | 8/1970 | Boutsicaris et al. | 560/241 |
| 4,044,041 | 8/1977 | Stapp | 560/241 |
| 4,424,388 | 1/1984 | Braithwaite et al. | 568/895 |
| 4,450,289 | 5/1984 | Paxson | 560/241 |

OTHER PUBLICATIONS

Bulletin of the Institute of Chemical Research, Kyoto University 1972, 50(4), pp. 836-867.

*Primary Examiner*—Werren B. Lone
*Attorney, Agent, or Firm*—Rupert B. Hurley, Jr.; David L. Hedden

[57] ABSTRACT

Process for the preparation of unsaturated alcohols and/or esters thereof by reacting conjugated dienes with water and/or aqueous carboxylic acid solutions in the presence of a macroporous acid ion exchanger and suitable solvents. The diene has the general formula I

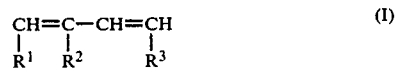

in which $R^1$, $R^2$ and $R^3$ are hydrogen or a methyl group and $R^2$ also can represent an aliphatic hydrocarbon radical having 2 to 6 carbon atoms which may contain a double bond which is not in a conjugated position relative to the double bonds of the diene, and preferably $R^1$ and $R^3$ each represent groups $CH_3$ or $CH_2$—$CH_3$. Said diene is reacted in a homogeneous or quasi-homogeneous phase in the presence of said macroporous acid ion exchanger.

4 Claims, No Drawings

PROCESS FOR THE PREPARATION OF UNSATURATED ALCOHOLS AND/OR ESTERS THEREOF

BACKGROUND OF THE INVENTION

1. Field of the Invention

The invention relates to an improved method for the preparation of unsaturated alcohols and/or esters thereof by reacting conjugated dienes with water and/or aqueous carboxylic acid solutions in the presence of a macroporous acid ion exchanger.

2. Description of the Prior Art

Unsaturated alcohols and esters thereof are desirable intermediate products which play an important part, for example, in the synthesis of natural products such as terpenes. Therefore, there have been a number of attempts to find advantageous processes for their preparation. Thus, for example, the addition of carboxylic acids to conjugated dienes was examined in the presence of sulfuric acid (compare Ber. 76, (1943), 831) and catalysts such as $PdCl_2/CuCl_2$ (compare the Bulletin of the Japanese Petroleum Institute 13 (1971) 73, Austrian Journal of Chemistry 1571, (1971), 24). However, the reactions are very nonspecific.

Another known method for the preparation of 2-methyl-3-butene-2-ol is the addition of hydrogen chloride to isoprene whereupon the reaction products are hydrolyzed in an alkaline medium (compare German Published Application 30 21 414), or a neutral medium (compare German Application 23 19 761). Drawbacks of these methods are the large salt production, multiple stages of the preparation process, as well as very pronounced corrosion problems.

Another method is known according to which 2-methyl-3-butene-2-ol is produced by reaction of acetylene with acetone and subsequent partial hydrogenation (compare M. De Malde, Chim. e Ind. (Milan) 45 (1963), page 665 and the following). However, acetylene is expensive and technically not simple to handle.

Also described in the prior art is the two-phase reaction of isoprene with water in tetrahydrofuran (THF) in the presence of the gel ion exchanger Amberlite ® IR 120 (compare Bulletin of the Institute of Chemical Research, Kyoto University 1972, 50 (4), pages 863–7). However, in spite of temperatures of 80° to 110° C. and reaction times of up to 10 hours, this method resulted only in reactions of 7 percent maximum.

Therefore the purpose of this invention was to improve the method for the preparation of unsaturated alcohols and esters thereof by reacting conjugated dienes with water and/or with aqueous carboxylic acid solutions in such a manner that the desired compounds are achieved in a simple manner and with good yield in a single-stage process.

Surprisingly, it was found that the mentioned reaction at low temperatures with shorter reaction times results in a considerably higher reaction and higher yield than in the known method if the reaction is carried out in a homogeneous or quasi-homogeneous phase with suitable solvents in the presence of a macroporous acid ion exchanger.

SUMMARY OF THE INVENTION

This invention relates to a method for the preparation of unsaturated alcohols and/or esters thereof by reacting conjugated dienes with water and/or aqueous carboxylic solutions in the presence of a macroporous acid ion exchanger as well as suitable solvents. The diene has the general formula I

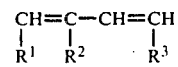

which $R^1$, $R^2$ and $R^3$ are hydrogen or a methyl group, and $R^2$ also can represent an aliphatic hydrocarbon radical having 2 to 6 carbon atoms which can contain a double bond which is not in a conjugated position to the double bonds of the diene and preferably $R^1$ and $R^3$ each represent the groups $CHhd 3$ or $CH_2$—$CH_3$. Said diene is reacted in a homogeneous or quasi-homogeneous phase in the presence of said macroporous acid ion exchanger.

DETAILED DESCRIPTION OF THE INVENTION

The method of this invention is particularly advantageous (1) if at least one of acetone, dioxane, or a cyclic or noncyclic sulfone, particularly sulfolane, is used as a solvent; (2) if water is added; and (3) if the addition of water as well as that of the acid is carried out in the presence of macroporous acid sold under the trademarks Lewatit ® SPC 118, Lewatit SP 112, or Amberlyst ® XN 1010.

Suitable conjugated dienes include buta-1,3-diene, isoprene, cyclopentadiene, cyclohexa-1,3-diene, and myrcene (2-vinyl-5-methylhexa-1,4-diene). Isoprene is particularly suitable. Suitable solvents are polar aprotic solvents which are capable of forming a homogeneous phase under the reaction conditions with diene and water and/or the aqueous carboxylic acid solution or a quasi-homogeneous phase when a solubilizer is added. Single-phase, true solutions as are obtained, for example with acetone, dioxane, tetrahydrofuran and cyclic or noncyclic sulfones such as sulfolane, sulfolene, dimethylsulfone and sulfonal and mixtures of these liquids are preferred. Particularly advantageous is the use of solvents which boil at a higher temperature than the resultant unsaturated alcohol and/or esters thereof since processing of the reaction mixture is more economical. Such solvents are, for example, the sulfones, particularly sulfolane. The solvent concentration advantageously is 50 to 90 volume percent, particularly 60 to 70 volume percent.

Since observations to date have shown it to be important that the reaction of the diene with the water and/or aqueous carboxylic acid on the ion exchanger takes place in a homogeneous or quasi-homogeneous phase, it is not necessary that the entire liquid be a single-phase substance. It is rather sufficient if a solvent with limited water solubilty is used since a diene-water-solvent phase is obtained in this case in addition to a second phase. Suitable solvents include diethyl ether or methyl-ethyl ketone.

Instead of reaction in a truly homogeneous molecular dispersed phase, the reaction can also be carried out in a quasi-homogeneous phase, that is, a phase which acts like a homogeneous phase as a result of the degree of dispersion. This expands the number of suitable solvents to those which are not soluble in water or which have a limited solubility in water. In this case, for example when using higher ethers such as methyl-tertiary butylether, an inert surface-active compound is used as a solubilizer in a known fashion.

It is understood that the solvents in general should be inert or largely inert with respect to all reactants under the reaction conditions. In the case of the use of an acid as a reactant, the acid usually acts as a solvent, with the aid of which a homogeneous phase forms. The mole ratio of water to diene advantageously is generally 5 to 25, preferably 15 to 20. The diene conversion degree increases with increasing mole ratios.

Aqueous carboxylic acid solutions are used for the preparation of esters. Preferably used are solutions of lower aliphatic carboxylic acids, such as acetic acid and propionic acid. Advantageously, the acid concentration in the aqueous solutions containing the solvent is generally 50 to 90 volume percent, preferably 70 to 80 volume percent.

The macroporous acid ion exchangers to be used in accordance with this invention are predominantly sulfonated crosslinked copolymers based on styrene and divinyl benzene as the matrix which have a macroporous structure similar to that of the classic adsorption media, $Al_2O_3$, $SiO_2$, or activated charcoal, as a result of specific preparation methods. This porous structure is generally constant, that is, independent of the reaction medium, and the swelling brought about thereby. By this characteristic the macroporous resins differ from the previously known exchangers with gel-like properties. The resins to be used in accordance with this invention have an average pore diameter of greater than 50 Angstrom and an internal surface determined according to Brunauer, Emmet and Teller ("BET"-surface) which is larger than one square meter per gram.

Greater details on the properties and determination methods of macroporous ion exchangers are contained in the pamphlet A.R. Pitochelli, "Ion Exchange Catalysis and Matrix Effects" (published 1974) by Rohm and Haas in Philadelphia. Additional literature references are R. Kunin, "Amber-hi-lites; Catalysis with Ion Exchange Resins," 1972, and R. Kunin and R. Hetherington, "A Progress Report on the Removal of Colloids from Water by Macroreticular Ion Exchange Resins," 1969, both also published by Rohm and Haas.

Suitable macroporous acid ion exchangers have been commercially available for some time. Examples include products sold under the trademarks Lewatit SPC 118 and SP 112, Amberlyst 15, XN-1005 and XN 1010, Dowex ® HGR and MSC-1 and Kastel ® C 350 P and C 386. The cation exchangers are used in the usual commercially available H(+) form.

The optimum temperature for the reaction according to this invention is very much dependent upon the diene used. Thus, for example, the optimum temperature for the hydration of isoprene is 35° C. to 45° C. and that for butadiene is 80° C. to 110° C. Depending upon the diene, the reaction temperatures generally vary from 0° to 150° C., preferably between 20° C. and 120° C. The reaction generally takes place under the vapor pressure of the diene at the corresponding reaction temperature. With the use of advantageous temperature ranges, the reaction time generally amounts to 0.2 to 10 hours, particularly 2 to 6 hours, with batch-type working conditions. Depending upon the diene used, the total yield is 40 to 45 percent with overall yields for unsaturated alcohol and/or esters thereof between 80 and 85 percent.

In the case of an unsymmetrical diene, for example, isoprene, the addition of water and/or an acid can take place as a 1,2-, 3,4- and 1,4-addition. The hydroxyl group and/or the ester grouping can form in the 1-, 2-, 3- and 4-position. However, corresponding with known laws, these possibilities are restricted because tertiary and then secondary alcohols and/or esters are preferentially formed before the primary alcohols and/or esters thereof. Because of the reactivity of the conjugated system, the reaction initially stops after the monoaddition so that one is in a position to largely suppress the bis-additions. Based on the said laws, predominantly one of the possible process products is obtained. Since, however, all resultant unsaturated alcohols and/or esters thereof are valuable compounds, it is desirable to add the individual yields to obtain a total yield in order to illustrate the success of the process.

Unreacted diene can be separated from the reaction mixture by distillation and can be used again. The resultant alcohols and/or the alcohols and esters thereof can be isolated from the aqueous diene-free reaction mixture in a known fashion. The water/solvent mixture also can be used again for the reaction.

The process of this invention easily can be made continuous, which is particularly advantageous. Using this process, the unsaturated alcohols and/or esters thereof which are very much in demand as intermediate products, can be produced in a simple, environmentally sound manner with good yields.

The following examples illustrate the various aspects of the invention but are not intended to limit its scope. Where not otherwise specified throughout this specification and claims, temperatures are given in degrees centigrade and parts, percentages and proportions are by weight.

EXAMPLE 1

In an autoclave equipped with an agitator, a homogeneous solution consisting of 56 grams (0.8 moles) isoprene and 1000 milliliters of a 65 volume percent aqueous sulfolane solution were reacted in the presence of 50 grams of a cation exchanger sold under the trademark Lewatit SPC 118 at a temperature of 40° C. For this reaction the mole ratio of water to isoprene was 24 to 1. After agitating at 40° C. for 4 hours, 40 percent of the solution mixture had reacted. The yield of 2-methyl-3-butene-2-ol was 73 percent, and that of 3-methyl-2-butene-1-ol (Prenol) was 10%.

EXAMPLE 2

In accordance with Example 1, a homogeneous solution of 6.2 grams (0.11 moles) of butadiene and 100 milliliters of a 65 volume percent aqueous sulfolane solution were reacted in the presence of a cation exchanger sold under the trademark Lewatit SPC 118 at a temperature of 100° C. After agitating at 100° C. for 6 hours, 76 percent of the mixture had reacted. A yield of 60 percent 1-butene-3-ol and a yield of 26 percent 2-butene-1-ol (crotylalcohol) was obtained.

EXAMPLE 3

Analogous with Example 1, a homogeneous solution of 5.6 grams (0.08 moles) of isoprene and 10 milliliters of a 75 volume percent aqueous acetic acid solution was reacted at 40° C. in the presence of 5 grams of a cation exchanger sold under the trademark Lewatit SPC 118 (mole ratio of acetic acid to isoprene 15.6 to 8.7; mole ratio of water to isoprene=17.3). After stirring at 40° C. for 6 hours, the reaction was 73 percent complete. There was obtained 2-methyl-3-butene-2-ol with a yield of 48 percent, Prenol with a yield of 2 percent, and prenylacetate with a yield of 30 percent.

EXAMPLE 4

Analogous with Example 1, a solution of 5.6 grams (0.08 moles) of isoprene and 100 milliliters of a 65 volume percent aqueous propionic acid (mole ratios: water to isoprene=24.3, propionic acid to isoprene=10.7) was reacted in the presence of 5 grams of a cation exchanger sold under the trademark Lewatit SPC 118 at 35° C. After stirring at 35° C. for 6 hours, the reaction was 20 percent complete. There was obtained 2-methyl-3-butene-2-ol with a yield of 57 percent and prenylacetate with a yield of 29 percent.

EXAMPLE 5

Analogous with Example 1, a solution of 6.2 grams (0.11 moles) of butadiene was reacted with 100 milliliters of an 80 volume percent aqueous acetic acid solution in the presence of 5 grams of a cation exchanger sold under the trademark Lewatit SPC 118 at a temperature of 80° C. After stirring at 80° C. for 6 hours, the reaction was 48 percent complete, with the following product distribution:
1-butene-3-ol (13%)
1-butene-3-ol-acetate (30%)
crotylalcohol (9%)
crotylacetate (40%)
overall yield: 92%

EXAMPLE 6

(Comparison example, forming no part of this invention)

The procedure and proportions were those described in Example 5 except that pure acetic acid was used instead of the aqueous acetic acid used in Example 5. After stirring for 6 hours at 80° C. the conversion of butadiene was 94 percent, but the total yield however was only 37 percent.

EXAMPLES 7–9

Analogous to Example 1, a homogeneous solution of 65 volume percent of sulfolane, 10 volume percent isoprene, and 25 volume percent of water was in each example mixed with 5 grams of the ion exchanger shown in the table below. The mixture was subsequently heated to 40° C. while being stirred for a period of 4 hours. The achieved isoprene conversion, as well as the yield of 2-methyl-3-butene-2-ol and prenol are listed in the following table.

EXAMPLES 10–15

(Control examples forming no part of this invention)

Analogous with Examples 7–9, the same procedure and proportions were used except for the use of 5 grams of the ion exchanger shown in the table below. Results are also listed in the below table.

While this invention has been described with reference to certain specific embodiments, it will be recognized by those skilled in the art that many variations are possible without departing from the scope and spirit of the invention and it will be understood that it is intended to cover all changes and modifications of the invention disclosed herein for the purposes of illustration which do not constitute departures from the spirit and scope of the invention.

TABLE

| Example | Ion Exchanger | Isoprene Conversion (%) | 2-methyl-3-butene-2-ol (%) | prenol (%) |
|---|---|---|---|---|
|  | Macroporous |  |  |  |
| 7 | Lewatit SPC 118 | 40 | 73 | 12 |
| 8 | Lewatit SP 112 | 25 | 59 | 12 |
| 9 | Amberlyst XN 1010 | 23 | 67 | 9 |
| Control Example | Gel |  |  |  |
| 10 | Amberlite JR 120 | 7 | 64 | 9 |
| 11 | Amberlite XE 365 A |  |  |  |
| 12 | Nafion ® |  |  |  |
| 13 | Dowex 50 WX | <5 | not determined |  |
| 14 | Lewatit S 100 |  |  |  |
| 15 | Dowex HER W2 |  |  |  |

The embodiments of the invention in which an exclusive property or privilege is claimed are defined as follows:

1. A process for the preparation of unsturated alcohols and/or esters thereof by reacting conjugated dienes with water and/or aqueus lower aliphatic carboxylic acid solutions in the presence of a macroporous acid ion exchanger having an average pore diameter greater than 50 Angstrom, and a polar aprotic solvent, wherein a diene having the general formula I

$$CH=C-CH=CH \quad \quad (I)$$
$$\;\;|\;\;\;\;\;|\;\;\;\;\;\;\;\;\;\;|$$
$$R^1\;\;R^2\;\;\;\;\;\;R^3$$

in which $R^1$, $R^2$ and $R^3$ represent hydrogen or a methyl group and $R^2$ also can represent an aliphatic hydrocarbon radical having 2 to 6 carbon atoms which may contain a double bond which is not in a conjugated position relative to the double bonds of the diene, is reacted in a homogeneous or quasihomogeneous phase.

2. The process of claim 1 wherein at least one of a solvent selected from the group consisting of acetone, dioxane, and a cyclic or noncyclic sulphone is used, $R^1$ and $R^3$ each represent $CH_3$ or $CH_2-CH_3$ groups and wherein water is added to the dienes of formula I.

3. The process of claim 2 wherein said solvent is sulfolane.

4. The process of claim 1 wherein said macroporous ion exchanger is selected from the group consisting of an ion exchanger sold under the trademark Lewatit ® SPC 118, Lewatit SP 112 or Amberlyst ® XN 1010.

* * * * *